United States Patent
Smith

[11] Patent Number: 5,376,089
[45] Date of Patent: Dec. 27, 1994

[54] ELECTROSURGICAL INSTRUMENT

[75] Inventor: Roger F. Smith, Boulder, Colo.

[73] Assignee: Conmed Corporation, Utica, N.Y.

[21] Appl. No.: 100,363

[22] Filed: Aug. 2, 1993

[51] Int. Cl.$^5$ .................................. A61B 17/39
[52] U.S. Cl. ......................... 606/42; 606/45; 606/49; 200/505
[58] Field of Search .............. 606/41, 42, 45, 48–50; 200/505

[56] References Cited

U.S. PATENT DOCUMENTS

| | | |
|---|---|---|
| 2,808,833 | 10/1952 | August. |
| 3,902,494 | 9/1975 | Haberlen et al. |
| 3,906,955 | 8/1975 | Roberts. |
| 4,032,738 | 6/1977 | Esty et al. ........................ 606/42 |
| 4,034,761 | 7/1977 | Prater et al. ..................... 606/42 |
| 4,427,006 | 1/1984 | Nottke et al. .................... 606/42 |
| 4,625,723 | 12/1986 | Alnether et al. ................ 606/42 |
| 4,683,884 | 8/1987 | Hatfield et al. |
| 4,719,914 | 1/1988 | Johnson. |
| 4,919,129 | 4/1990 | Weber, Jr. et al. |
| 4,932,952 | 6/1990 | Wojciechowicz, Jr. |
| 4,936,301 | 6/1990 | Rexroth et al. |
| 5,071,418 | 12/1991 | Rosenbaum. |
| 5,080,660 | 1/1992 | Buelna. |
| 5,084,045 | 1/1992 | Helenowski. |
| 5,085,657 | 2/1992 | Ben-Simhon. |
| 5,088,997 | 2/1992 | Delahuerga et al. |
| 5,122,138 | 6/1992 | Manwaring. |
| 5,154,709 | 10/1992 | Johnson. |
| 5,160,334 | 11/1992 | Billings et al. |
| 5,167,659 | 12/1992 | Ohtomo et al. |
| 5,190,542 | 3/1993 | Nakao et al. |
| 5,192,267 | 3/1993 | Shapira et al. |
| 5,217,457 | 6/1993 | Delahuerga et al. |
| 5,224,944 | 7/1993 | Elliott. |
| 5,226,904 | 7/1993 | Gentelia et al. ................ 606/42 |
| 5,256,138 | 10/1993 | Burek et al. .................... 606/42 |

FOREIGN PATENT DOCUMENTS

| | | | |
|---|---|---|---|
| 181733 | 5/1986 | European Pat. Off. ........ 606/42 |
| 2094555 | 9/1982 | United Kingdom ........... 200/505 |

Primary Examiner—Lee S. Cohen
Attorney, Agent, or Firm—Larson & Taylor

[57] ABSTRACT

A simple and reliable electrosurgical instrument includes a cable having a main contact wire and first and second insulated switch wires. The cable is received into a main member having three electrical terminals to secure the three wires to three electrically isolated conducting strips which are mounted longitudinally in a fluid-sealed switch assembly. The main contact wire is connected to the main conducting strip, and the first and second switch wires are connected to the first and second switch conducting strips. The main conducting strip permanently connects the main contact wire to a socket which receives a electrode blade. A switch device selectively connects the main conducting strip to one of the two switch conducting strips. When a user pushes one of two buttons mounted on the outside of the electrosurgical instrument, the instrument provides a cutting current or a coagulation current.

23 Claims, 4 Drawing Sheets

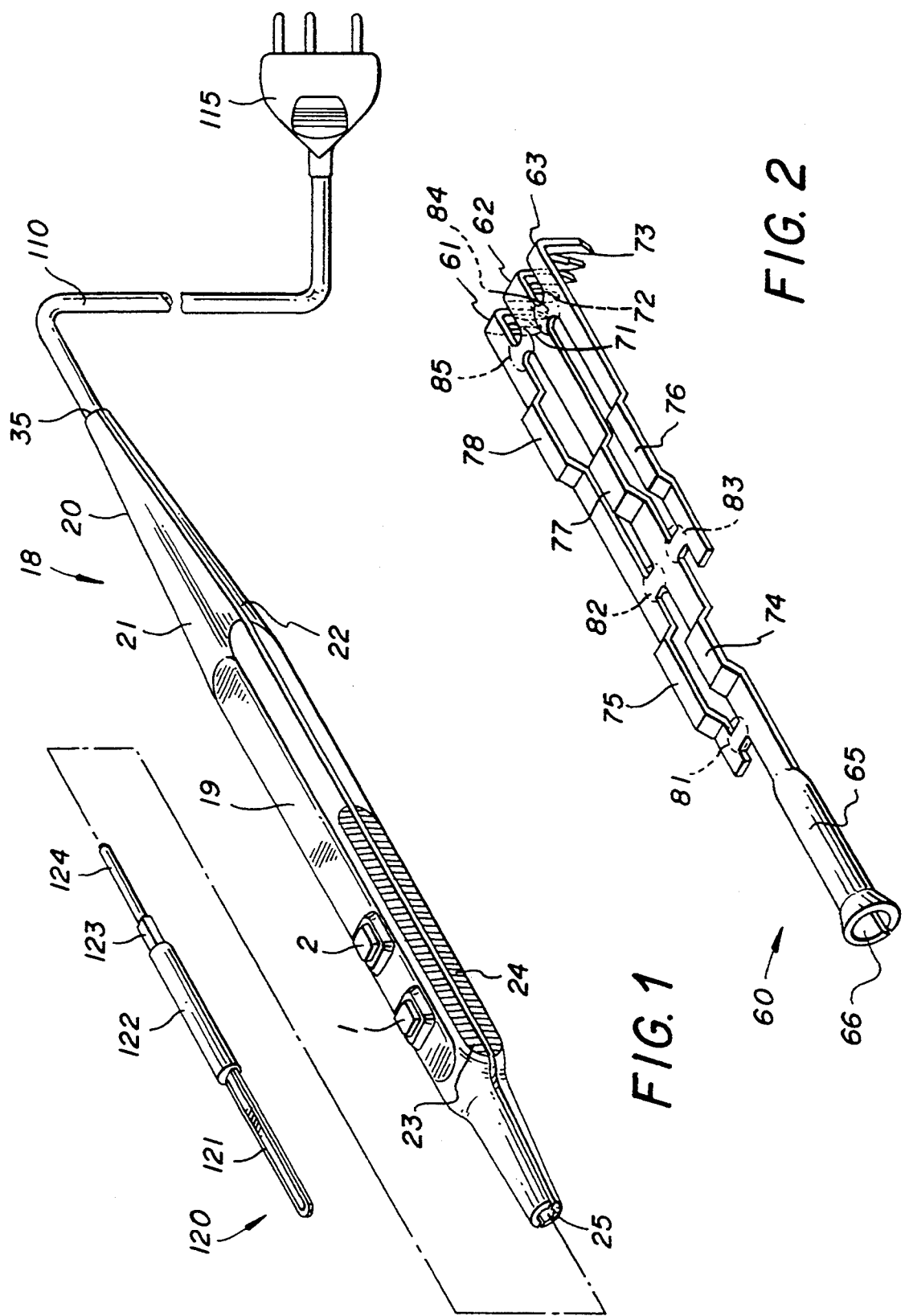

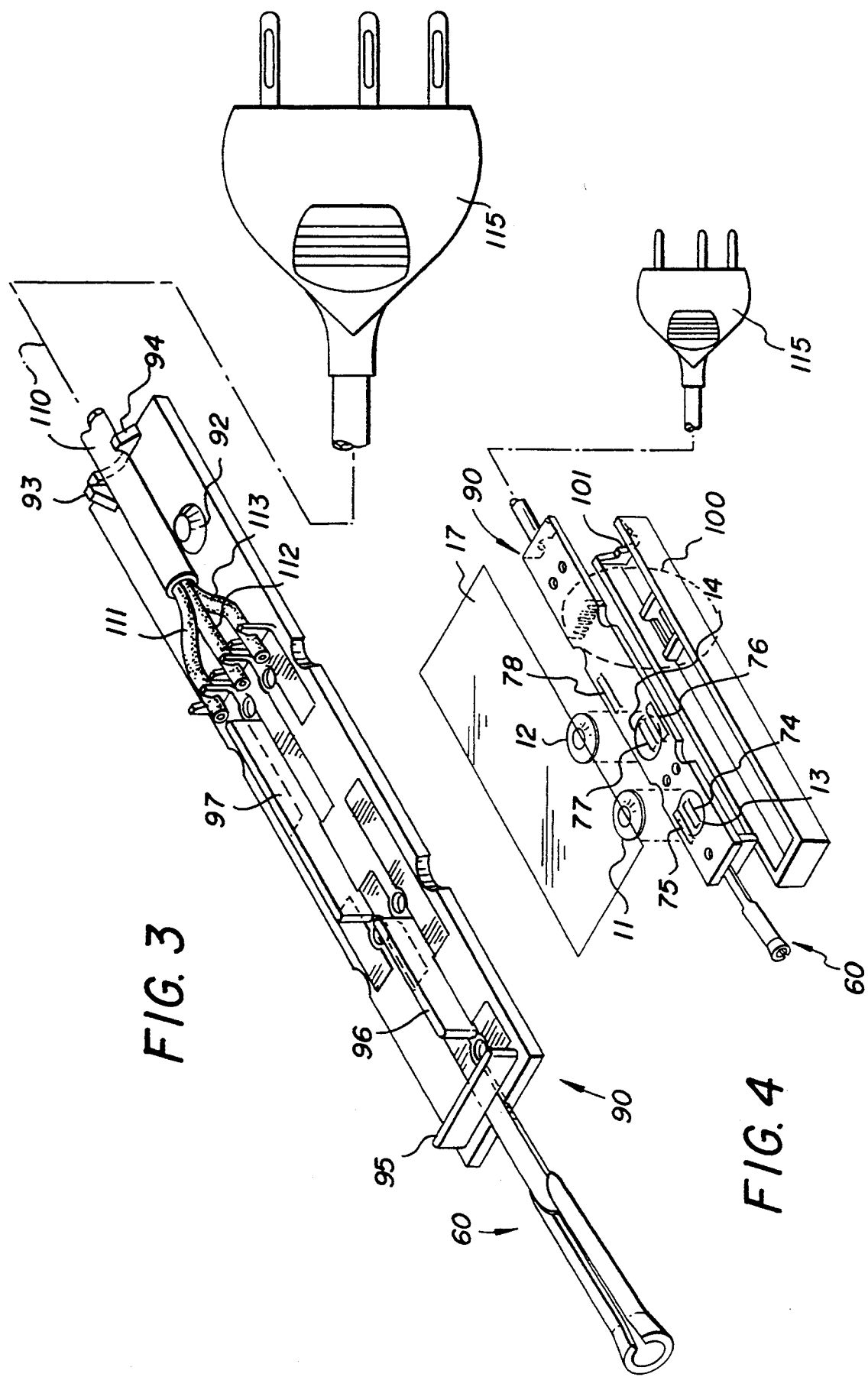

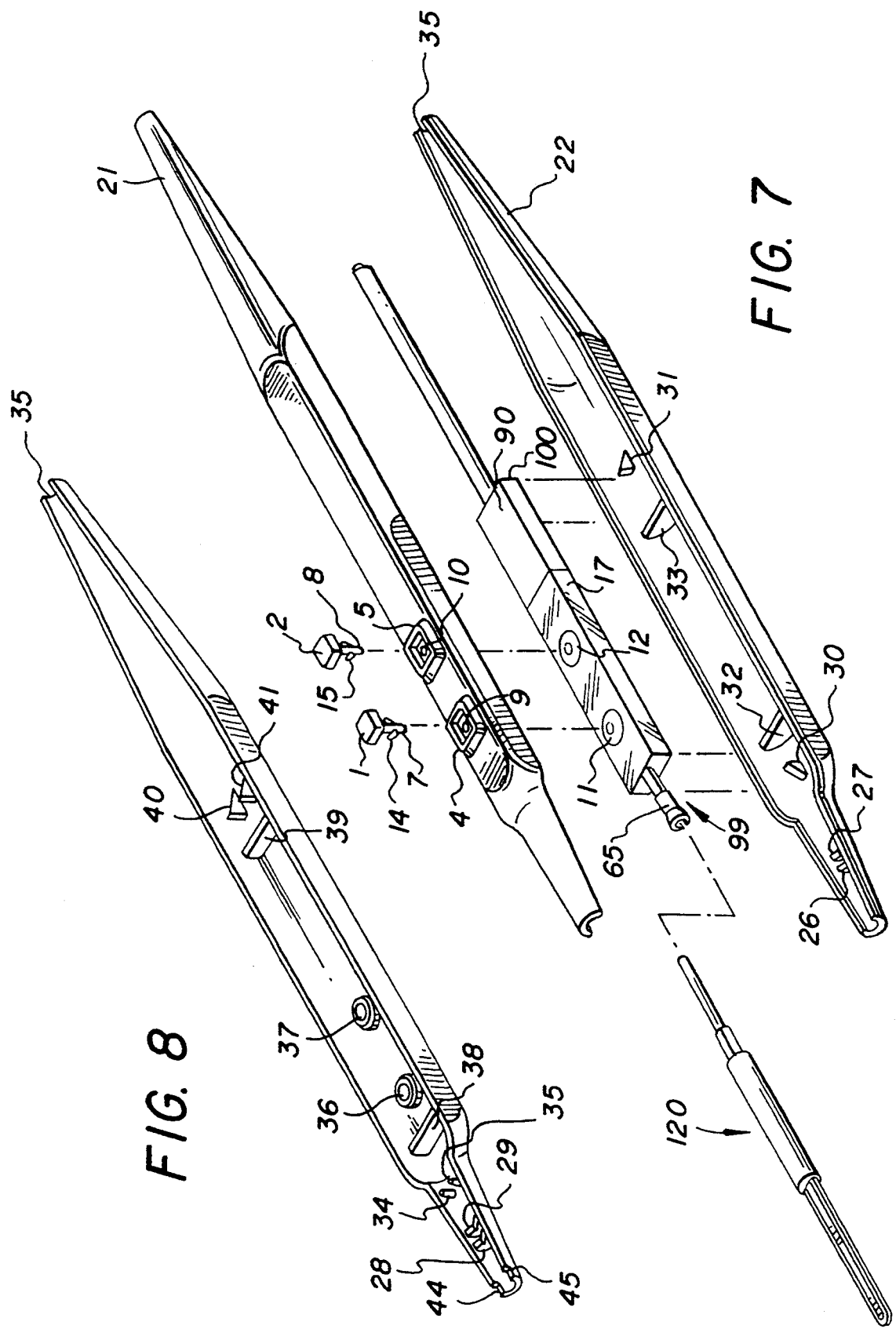

ELECTROSURGICAL INSTRUMENT

FIELD OF THE INVENTION

The present invention relates generally to electrosurgical instruments, and more particularly to a simple, reliable and inexpensive electrosurgical instrument.

BACKGROUND OF THE INVENTION

Electrosurgical instruments are known in the art and are used for electrosurgery. Typically, a suitable electrical generator provides a high frequency or radio frequency signal which is transmitted to a small surgical electrode having a thin knife-like tip which is applied to a patient. The patient is grounded to a patient plate, with the plate being connected by a further conductor back to the generator. The relatively small area of contact by the electrode with the patient provides an intense current in a highly localized area, producing a cutting action. The current then passes through the patient's body at the patient plate wherein the area of contact is large enough that no burning occurs at this location.

For cutting purposes, the generator is activated to produce a continuous signal, typically a sine wave signal. However, the same instrument may also be applied to the wound after cutting in order to produce coagulation. This coagulation is produced by a pulsing signal from the generator. Switching means are thus needed for the operator to switch between the two types of electrical energy produced by the generator.

Although a number of arrangements have been devised for selectively activating the electrical energy, the most satisfactory of these arrangements is a multiple wire cable conductor extending from the generator to the electrode. One conductor is normally connected to the electrode and two other conductors are selectively connectable to the therapeutic current conductor through switches to complete circuits back to the activating means for causing the generator to produce the desired mode of current.

Electrosurgical instruments found to be particularly safe and effective for surgical applications are those which incorporate finger activated switches, those which allow for readily interchangeable electrodes, those which are water resistant, and those which are thin and properly balanced for close surgical use where a certain feel is necessary. Such instruments are typically described as an electrosurgical pencil. However, such prior instruments have had many disadvantages in that the electrode connections were expensive to achieve, failed to provide a positive connection, and/or were subject to wear problems.

Disclosed in U.S. Pat. No. 4,032,738 (Esty et al.) is an electrosurgical instrument providing dome switches on the handle of the instrument to allow manual selection of cutting or coagulation signals from an electrosurgical generator. The instrument is generally flat to retain the feel of a nonelectrical surgical instrument.

U.S. Pat. No. 4,034,761 (Prater) discloses a disposable electrosurgical unit for applying either cutting signals or coagulation signals by the actuation of a switch in the handle of the unit. In particular, operation of the switch deforms a resilient conducting member which is electrically connected to the electrode blade, such that pushing the switch in one direction connects the resilient member to one electrosurgical energy source, and pushing the switch in the other direction connects the resilient member to another energy source, thereby conducting the selected electrosurgical energy to the patient.

U.S. Pat. No. 4,427,006 (Nottke) discloses an electrosurgical instrument providing an advantageous interface between an electrosurgical electrode and an electrosurgical generator. In particular, the wires of the cable are supported on a flat insert, and control pins are forced through the insulation of these wires. A conductor plate with cantilevered conductor strips lies over the insert and these strips are selectively connected to the contact pins by use of dome spring push buttons.

U.S. Pat. No. 4,625,723 (Altnether et al.) discloses an electrosurgical instrument including complex push button switches used to selectively bridge electrically isolated circuit contacts to apply either cutting or coagulation signals to a patient.

Other U.S. patents of general interest disclosing electrosurgical instruments include the following: U.S. Pat. No. 4,619,258 (Poole), U.S. Pat. No. 4,872,254 (Duliveria et al.), U.S. Pat. No. 4,492,832 (Taylor), U.S. Pat. No. 4,922,903 (Welch et al.), and U.S. Pat. No. 4,911,159 (Johnson et al.).

SUMMARY OF THE INVENTION

In accordance with the present invention, a simple and reliable electrosurgical instrument is provided. This instrument delivers electrical energy from an electrosurgical generator to a patient for cutting, coagulation, and the like.

The instrument includes an electrode blade and a cable which is electrically connected to the electrosurgical generator. The cable includes a main insulated contact wire, and first and second insulated switch wires. This cable is received in a circular aperture at the rearward end of a hollow body that serves as a handle for the electrosurgical instrument. A switch assembly inside this hollow body provides means to selectively conduct various types of electrosurgical energy between the switch wires and the electrode blade. The switch assembly includes three conducting strips. The rearward end of each of the conducting strips includes means to remove the insulation from a portion of one of the insulated wires during assembly of the electrosurgical instrument, and includes holding means to hold the uninsulated portion of the wire adjacent to the conducting strip, thereby electrically connecting the conducting strip to one of the wires. The main conducting strip provides a permanent electrical connection between the main contact wire and a blade receiver, which is positioned near the forward end of the electrosurgical instrument. The electrode blade is inserted into a circular aperture in the forward end of the hollow body and is also resiliently received into a circular terminal in the blade receiver. The first and second switch conducting strips are electrically connected to the two switch wires, and two buttons on the outside of the hollow body provide means to electrically connect the first or second switch conducting strips to the main conducting strip, thereby transmitting a selected electrical energy to the electrode blade from the electrosurgical generator.

In a preferred embodiment, the blade receiving terminal, the three conducting strips, the wire insulation removal means, and the wire holding means are stamped from a single sheet of metal. Portions of the conducting strip are raised and serve as the electrical contacts for the switching means. The metal stamping is overmolded with thermoplastic, thereby creating a switch on the top surface of which the raised electrical contacts are the only exposed conductors. The switch is then punched at several punch points to electrically isolate each conducting strip from the other conducting strips. The wire insulation removal means and the wire holding means are both accomplished by the use of insulation displacement terminals created in the original metal stamping.

In the preferred embodiment, two dome-shaped members are mounted in circular depressions on the top surface of the switch such that each dome-shaped member is in permanent electrical contact with a separate electrical contact on the main conducting strip. Two buttons mounted on the top surface of the electrosurgical instrument have cylindrical tips which protrude downward through apertures in the top surface of the instrument. When pressure is applied to one of the buttons, the protruding cylindrical tip of the button presses against the center of one of the dome-shaped members, deforming the member such that electrical contact is made between the first or second switch conducting strips and the main conducting strip, thereby transmitting a selected electrical energy to the electrode blade from the electrosurgical generator.

In the preferred embodiment, sealing tape is applied over the top surface of the switch to fluid seal the dome-shaped members and the raised electrical contacts from the external environment, and to secure the dome-shaped members within the circular depressions.

In the preferred embodiment, a switch cover is ultrasonically welded to the bottom of the switch to form a switch assembly which is fluid sealed from the external environment. The cable extends through a circular aperture at the rear of the switch assembly, and is ultrasonically welded between the switch and switch cover to further seal the switch assembly. The upper surface of the cover includes three upstanding ridges which force the uninsulated portions of the wires to remain within the holding means on the lower surface of the switch- The upper surface of the cover also includes two upstanding ridges which press the three insulated wires against the lower surface of the switch, thereby providing strain relief means to ensure that the wires are not inadvertently removed from the wire holding means.

In the preferred embodiment, the hollow handle of the electrosurgical instrument is formed from an upper handle member and a lower handle member which are welded together ultrasonically. These upper and lower handle members contain various molded support members to ensure the proper alignment and orientation of the switch assembly within the hollow handle, both during and after assembly of the electrosurgical instrument.

In the preferred embodiment, the lower side of the upper handle member includes two electrode blade supports directly to the rear of the forward aperture of the hollow body, and the upper side of the lower handle member includes two additional electrode blade supports. After assembly of the hollow body from the upper and lower handle members, these blade supports create a hexagonal aperture. A portion of the electrode blade has a hexagonal cross-section which fits snugly into this hexagonal aperture when the electrode blade is inserted into the forward aperture of the hollow body, thereby preventing the electrode blade from inadvertently rotating relative to the hollow body during use of the electrosurgical instrument.

It is an advantage of the present invention that a very cost effective process may be utilized to manufacture the electrosurgical instrument. It is also an advantage of the present invention that an electrosurgical instrument having improved safety and reliability is produced.

It is a further advantage of the present invention that an electrosurgical instrument is produced having a limited number of parts which are easily assembled and several of which are available as standard commercial products.

Another advantage of the present invention is that the assembly of the electrosurgical instrument requires no soldering or crimping.

Still another advantage of the present invention is that the switch assembly of the electrosurgical instrument is completely sealed to fluid entry.

Yet another advantage of the present invention is that there are only two flexing parts, the dome switches used to make electrical contact between the electrosurgical generator and the tip of the electrode blade.

Other features and advantages of the present invention are stated in or apparent from a detailed description of presently preferred embodiments of the invention found hereinbelow.

BRIEF DESCRIPTION OF THE DRAWINGS

FIG. 1 is a schematic perspective view of an electrosurgical pencil in accordance with the present invention.

FIG. 2 is a schematic perspective view of the electrical contact which provides the conducting surfaces in the completed switch.

FIG. 3 is a schematic perspective view of the underside of the electrical switch.

FIG. 4 is a schematic perspective view of the upper side of the electrical switch along with the switch cover.

FIG. 7 is a schematic perspective view of a portion of the instrument depicted in FIG. 1 showing the connection of the buttons.

FIG. 8 is a schematic perspective view of the underside of the upper member of the hollow body of the handle of the electrosurgical instrument depicted in FIG. 1.

DETAILED DESCRIPTION OF THE PREFERRED EMBODIMENTS

Figure 5:
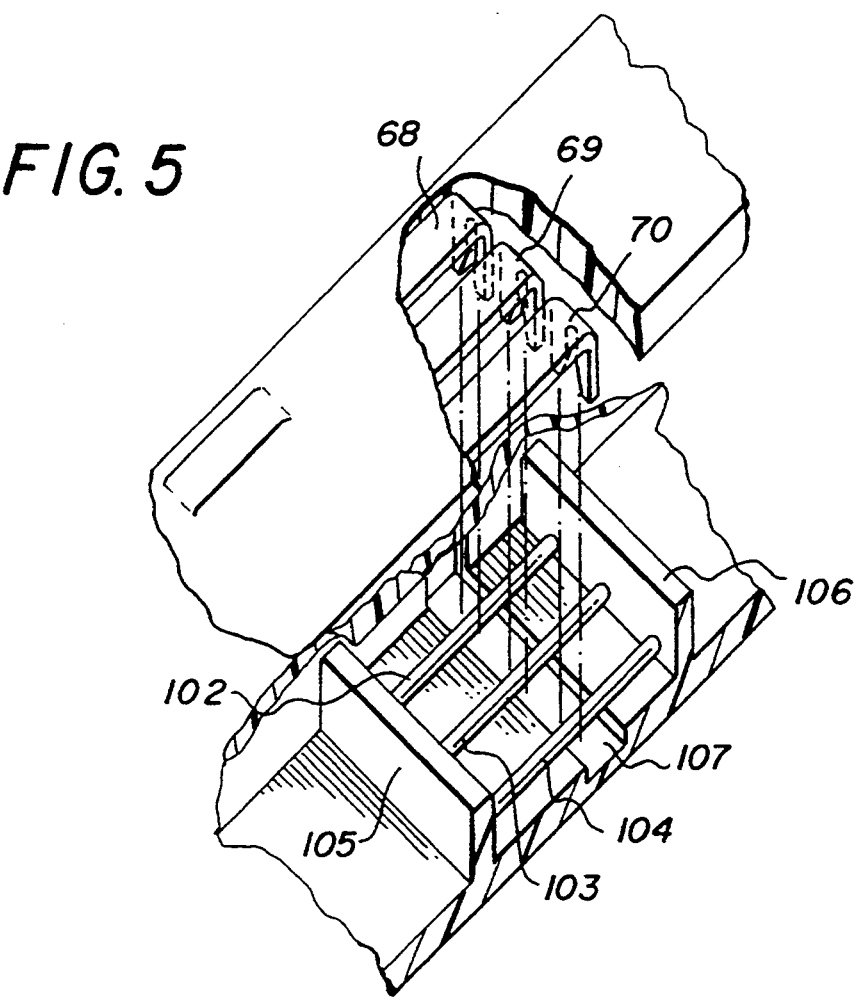
FIG. 5 is a schematic perspective view of the circled portion of FIG. 4.

With reference now to the drawings in which like numerals represent like elements throughout the views, an electrosurgical instrument or pencil 18 is depicted in FIG. 1. Preferably, electrosurgical instrument 18 includes a changeable electrode blade 120, a hollow elongate body 20 including an upper member 21 and a lower member 22, and a cable 110 which extends rearwardly from electrosurgical instrument 18 through an aperture 35 in hollow body 20. As typical of such devices in the art, cable 110 is connected to an electrosurgical generator and, as shown in FIG. 3 includes a main insulated contact wire 112, and first and second insulated switch wires 111 and 113. Upper member 21 is preferably ultrasonically welded to lower member 22 at all abutting surfaces after assembly.

FIG. 2 depicts electrical contact 60, which is preferably formed from a single metal stamping, and which includes a barrel terminal 65 with aperture 66 and conducting strips 61, 62, 63 which include insulation displacement terminals 71, 72, and 73 and electrical contacts 74, 75, 76, and 77 which are elevated with respect to the terminals 71, 72 and 73. As depicted in FIGS. 3 and 4, electrical contact 60 is overmolded with an insulating heat-resistant material such as thermoplastic to expose electrical contacts 74, 75, 76, and 77 on the upper surface of electrical switch 90. The switch 90 is stamped at five punch points 81, 82, 83, 84, and 85 to electrically isolate each of the conducting strips 61, 62, and 63.

Figure 6:
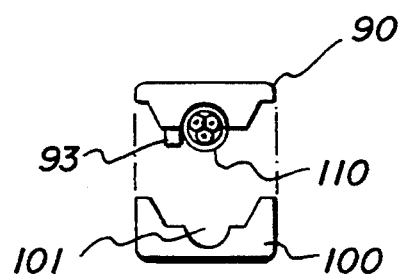
FIG. 6 is a rear elevation view of the switch and switch cover depicted in FIG. 4.

As best shown in FIG. 4, dome-shaped members 11 and 12 fit snugly into circular depressions 13 and 14 on the upper side of switch 90. Switch cover 100 is ultrasonically welded to the lower side of switch 90 to fluid seal the switch assembly from the external environment. Sealing tape 17 secures dome-shaped members 11 and 12 in circular depressions 13 and 14 and fluid seals electrical contacts 74, 75, 76, 77 and 78 from the external environment. As best shown in FIG. 6, cable 110 extends through aperture 101 formed at the intersection of switch 90 and switch cover 100. Cable 110 is ultrasonically welded between switch 90 and switch cover 100 to provide strain relief and to fluid seal switch assembly 99 from the external environment.

FIG. 5 depicts a cutaway view of the circled portion of FIG. 4. When switch 90 and switch cover 100 are welded together to form switch assembly 102, upstanding ridges 102, 103, and 104 force insulated wires 111, 112, and 113 into notches 68, 69, and 70. The notches 68, 69, and 70 are sized so the insulation is pinched off of wires 111, 112, and 113 in order to make electrical connections with conducting strips 61, 62, and 63. Upstanding members 105 and 106 force wires 111, 112, and 113 up against the underside of switch 90 to provide strain relief.

As best shown in FIGS. 4 and 7, electrosurgical instrument 18 includes switch means which selectively make electrical contact between main conducting strip 62 and first or second switch conducting strips 61 or 63. Yellow button 1 fits snugly into rectangular depression 4 on the top surface of upper body member 21, and button tip 7 extends down through aperture 9 and rests on top of dome-shaped member 11. Upwardly oriented flanges 14 allow for easy manual insertion of button 1 into aperture 9 but prevent accidental removal of the button. Sealing tape 17 holds the outer edge of dome-shaped member 11 in physical contact with electrical contact 75 at all times, but in its undeformed state, dome-shaped member 11 remains electrically isolated from electrical contact 74, whose length is smaller than the diameter of 11. When button 1 is pressed, however, button tip 7 forces dome-shaped member 11 to deform and make physical contact with electrical contact 74, thereby allowing electrical energy to flow to knife-like member 121 from the source of a cut signal within an electrosurgical generator. When button 1 is released, button-shaped member 11 returns to its original shape, and the current stops flowing. With reference to FIG. 3, upstanding ridges 96 and 97 on switch 90 prevent deformation of switch assembly 99 in response to pressure on button 1, thereby ensuring that dome-shaped member 11 will deform sufficiently to establish an electrical connection between contacts 74 and 75. The operation of blue button 2 is substantially identical to that of yellow button 1, except that an electrical connection is made between knife-like member 121 and a source of a coagulation signal within an electrosurgical generator.

Figure 9:
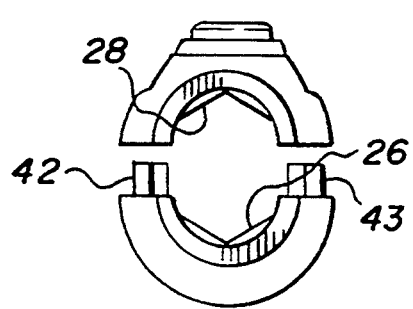
FIG. 9 is a front elevation view of the upper and lower members of the hollow body of the electrosurgical instrument depicted in FIG. 1.

With reference to FIGS. 7 and 8, switch assembly 99 is held in vertical position between support members 32 and 33 on the upper side of lower handle member 22, FIG. 7, and support members 38 and 39 on the lower side of upper handle member 21, FIG. 8. Triangular members 30 and 31, FIG. 7, on the upper side of lower handle member 22 prevent forward and backward motion of switch assembly 99 with respect to hollow body 20. Side to side motion of switch assembly 99 is prevented by the shape and inside dimensions of hollow body 20 itself. Doughnut-shaped members 36 and 37 abut flanges 14 and 15 on button tips 7 and 8 to hold buttons 1 and 2 within a certain elevation above the top surface of upper handle member 21. With reference to FIG. 9, raised inside edges 42 and 43 of lower handle member 22 align snugly with raised outer edges 44 and 45 of upper handle member 21, FIG. 8, to allow for simple and easy assembly of hollow body 20.

With reference to FIG. 8, terminal guides 34 and 35 ensure that barrel terminal 65, FIG. 7, remains in lateral position for insertion of cylindrical plug 124 of electrode blade 120 into terminal aperture 66. Four-sided electrode supports 26 and 27, FIG. 7, on lower handle member 22 and two-sided electrode supports 28 and 29, FIG. 8, on upper handle member 21 form a hexagonal aperture which secures hexagonal member 123, FIG. 1, on electrode blade 120 and prevents inadvertent rotation of knife-like member 121 during surgery.

Electrosurgical instrument 18 as described above allows for a very cost effective manufacturing process while improving both safety and reliability of the instrument. It will be appreciated that the electrosurgical instrument is comprised of only eleven main elements: upper handle member 21, lower handle member 22, electrode blade 120, switch 90, switch cover 100, cable 110, dome-shaped members 11 and 12, sealing tape 17, and buttons 1 and 2. It will be appreciated that several of these elements are standard components which are commercially available, allowing for savings and ready availability of parts. Electrosurgical instrument 18 may be manufactured inexpensively enough to be marketed as a single-use device, and it will be appreciated that a fixed blade may be used rather than removable electrode blade 120. However, it will also be appreciated that electrosurgical instrument 18 may also be manufactured and sold as a multiple-use device, and it will be noted that electrosurgical instrument 18 may be designed to allow for easy removal and replacement of electrode blade 120.

It will also be appreciated that switch assembly 99 is completely sealed to prevent fluid entry for safety and reliability during surgical operations. In particular, switch 90 is ultrasonically welded to switch cover 100, and cable 110 is fluid sealed between switch 90 and switch cover 100 in aperture 101. Also sealing tape 17 fluid seals all exposed conducting surfaces on switch assembly 99 (except the protruding barrel terminal 65, which is designed to conduct electrical energy to electrode blade 120). While these measures sufficiently ensure the electrical safety of electrosurgical instrument 18, further protection is provided by ultrasonically welding upper handle member 21 to lower handle member 22, welding cable 110 between handle members 21 and 22, and manufacturing aperture 25 and blade supports 26, 27, 28, 29 to provide a close fit for electrode blade 120.

It will be further appreciated that electrosurgical instrument 18 has a simple, durable, and reliable design. Only two flexing parts are present in instrument 18, dome-shaped members 11 and 12, and these parts are particularly well suited for repeated flexing without fatigue.

It will also be appreciated that electrosurgical instrument 18 is easy to assemble. The limited number of parts required to manufacture instrument 18 contributes to ease of assembly. Moreover, assembly is primarily manual, with the exception of ultrasonic welding of switch 90 to switch cover 100 and upper handle member 21 to lower handle member 22. Ease of manual assembly is further enhanced by self-aligning features of the components. In particular, cover guides 95 and 94 on switch 90 prevent reverse alignment of switch 90 and switch cover 100, and raised inner edges 42 and 43 of the lower handle member 22 and raised outer edges 44 and 45 of upper handle member 21 ensure ease of manual assembly of hollow body 20 prior to ultrasonic welding.

In addition to providing ease of assembly, electrosurgical instrument 18 is also easily tested both mechanically and electrically during assembly. Testing can be done just prior to attaching upper handle member 21 to lower handle member 22. This is particularly advantageous because there are no hidden assemblies or complex electrical contacts.

While the present invention has been described with respect to exemplary embodiments thereof, it will be understood by those of ordinary skill in the art that variations and modifications can be effected within the scope and spirit of the invention.

We claim:

1. An electrosurgical instrument for selectively providing electrical energy from an electrosurgical generator to a patient for cutting and coagulation, comprising:
   an electrode blade;
   a cable adapted to be connected to the electrosurgical generator, said cable including a main insulated contact wire, and first and second insulated switch wires;
   a main conducting strip connected electrically to said electrode blade, and first and second switch conducting strips which are selectively connectable to said main conducting strip;
   insulation displacement means for displacing a portion of the insulation from said main contact wire and said first and second switch wires, thereby exposing on each of said wires a short uninsulated portion;
   a first holding means for holding said uninsulated portion of said main contact wire adjacent to said main conducting strip, second holding means for holding said uninsulated portion of said first switch wire adjacent to said first switch conducting strip, and third holding means for holding said uninsulated portion of said second switch wire adjacent to said second switch conducting strip;
   a hollow elongate body including an upper handle member having upper and lower surfaces and a lower handle member having upper and lower surfaces to provide means for holding said electrosurgical instrument;
   a blade receiver within the elongate body resiliently receiving said electrode blade and electrically connected to said main contact wire to provide electrical connection between said main contact wire and said electrode blade, said electrode blade extending from the elongate body; and
   switch means within the elongate body for selectively connecting one of said first and second switch conducting strips to said main conducting strip such that a selected electrical energy is transmitted along said main conducting strip to said electrode blade from the generator via said main contact wire.

2. An electrosurgical instrument as claimed in claim 1 wherein the lower surface of said upper handle member includes blade receiver support members whereby said blade receiver is properly positioned to receive said electrode blade.

3. An electrosurgical instrument as claimed in claim 1 wherein the lower surface of said upper handle member and the upper surface of said lower handle member include electrode blade support members, and said electrode blade includes an electrode blade alignment member, such that said electrode blade, when fully inserted into said blade receiver, is prevented from rotating relative to said electrosurgical instrument.

4. An electrosurgical instrument as claimed in claim 1 wherein said upper and lower handle members include alignment means such that the two handle members may be easily and properly aligned during assembly of said electrosurgical instrument.

5. An electrosurgical instrument as claimed in claim 1 wherein said upper and lower handle members are welded together ultrasonically.

6. An electrosurgical instrument as claimed in claim 1 wherein said conducting strips and said blade receiver are stamped from a single metal sheet.

7. An electrosurgical instrument as claimed in claim 6 wherein said switch conducting strips are punched at various punch points to electrically isolate said conducting strips.

8. An electrosurgical instrument as claimed in claim 1 wherein said conducting strips include raised surfaces to serve as electrical contacts for said switch means.

9. A electrosurgical instrument as claimed in claim 8 wherein said conducting strips are overmolded with thermoplastic to create a switch having an upper and lower surface on the upper surface of which said electrical contacts are exposed.

10. An electrosurgical instrument as claimed in claim 9 wherein the upper surface of said switch includes first and second circular depressions in which first and second dome-shaped members are mounted such that each dome-shaped member is in permanent electrical contact with one of said electrical contacts on said main conducting strip, and such that (a) when downward pressure is applied near the center of said first dome-shaped member, electrical contact is made between said first dome-shaped member and one of said electrical contacts on said first switch conducting strip, and (b) when downward pressure is applied near the center of said second dome-shaped member, electrical contact is made between said second dome-shaped member and one of said electrical contacts on said second switch conducting strip.

11. An electrosurgical instrument as claimed in claim 10 wherein sealing tape is applied to the upper surface of said switch and over said dome-shaped members, such that (a) said electrical contacts and said dome-shaped members are fluid sealed from the external environment, and (b) said dome-shaped members are secured permanently within said circular depressions.

12. An electrosurgical instrument as claimed in claim 10 wherein first and second buttons are mounted on the upper surface of said upper handle member such that (a) a cylindrical tip attached to each button passes through a button aperture in said upper handle member, (b) the tip of said first button rests on said first dome-shaped member, (c) the tip of said second button rests on said second dome-shaped member, (d) when downward pressure is applied to said first button, said first dome-shaped member deforms sufficiently to make an electrical connection between said main and said first switch conducting strip, and (e) when downward pressure is applied to said second button, said second dome-shaped member deforms sufficiently to make an electrical connection between said main conducting strip and said second switch conducting strip.

13. An electrosurgical instrument as claimed in claim 12 including upwardly extending flanges on said tips of said first and second buttons such that (a) said tips are easily inserted manually through said button apertures, but (b) said buttons are not easily or inadvertently removed during use, transport, or handling of said electrosurgical instrument.

14. An electrosurgical instrument as claimed in claim 12 including first and second depressions on the upper surface of said upper handle member in which said buttons rest such that the motion of said buttons is substantially limited to vertical movement.

15. An electrosurgical instrument as claimed in claim 9 including a switch cover having upper and lower surfaces which attaches to the lower surface of said switch to create a switch assembly.

16. An electrosurgical instrument as claimed in claim 15 wherein the upper surface of said switch cover includes upstanding ridges to force said uninsulated portions of said wires to remain within said holding means.

17. An electrosurgical instrument as claimed in claim 15 wherein the upper surface of said switch cover includes strain relief members to ensure that said wires are not inadvertently removed from said holding means.

18. An electrosurgical instrument as claimed in claim 15 wherein the lower surface of said switch includes upstanding ridges to ensure the structural rigidity of said switch assembly.

19. An electrosurgical instrument as claimed in claim 15 wherein the lower surface of said switch includes upstanding cover guides to ensure that said switch cover is properly oriented and aligned with said switch during assembly of said switch assembly.

20. An electrosurgical instrument as claimed in claim 15 wherein the lower surface of said upper handle member and the upper surface of said lower handle member contain various support members to ensure that said switch assembly is properly oriented and aligned within said hollow body during after the assembly of said electrosurgical instrument.

21. An electrosurgical instrument as claimed in claim 15 wherein said switch assembly includes a circular aperture to receive said cable.

22. An electrosurgical instrument as claimed in claim 21 wherein the lower surface of said switch includes upstanding cable guides to ensure that said cable is aligned in said circular aperture during assembly of said electrosurgical instrument.

23. An electrosurgical instrument as claimed in claim 21 wherein said switch cover is attached to said switch by sealing means, and wherein said cable is secured within said circular aperture by sealing means, such that the inside of said switch assembly is completely sealed from external fluids.

* * * * *